(12) United States Patent
Reiderman et al.

(10) Patent No.: US 9,377,557 B2
(45) Date of Patent: *Jun. 28, 2016

(54) AZIMUTHALLY-SELECTIVE DOWNHOLE NUCLEAR MAGNETIC RESONANCE (NMR) TOOL

(71) Applicant: Halliburton Energy Services, Inc., Houston, TX (US)

(72) Inventors: Arcady Reiderman, Katy, TX (US); Songhua Chen, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/455,551

(22) Filed: Aug. 8, 2014

(65) Prior Publication Data

US 2015/0061665 A1 Mar. 5, 2015

Related U.S. Application Data

(60) Provisional application No. 61/872,362, filed on Aug. 30, 2013.

(51) Int. Cl.
*G01V 3/32* (2006.01)
*G01N 24/08* (2006.01)
(Continued)

(52) U.S. Cl.
CPC .............. *G01V 3/32* (2013.01); *G01N 24/081* (2013.01); *G01R 33/3678* (2013.01); *G01R 33/3808* (2013.01)

(58) Field of Classification Search
CPC ............ G01R 33/3808; G01R 33/445; G01R 33/448; G01R 33/543; G01R 33/3678; G01V 3/32; G01V 3/14; G01N 24/081; G01N 24/08; G01N 24/10

USPC .......................... 324/303, 307, 309, 318, 322
See application file for complete search history.

(56) References Cited

U.S. PATENT DOCUMENTS 4,629,986 A 12/1986 Clow et al.
5,280,243 A 1/1994 Miller
(Continued)

FOREIGN PATENT DOCUMENTS

GB 2324375 10/1998
GB 2419418 4/2006
(Continued)

OTHER PUBLICATIONS

Authorized Officer Jong Kyung Lee, PCT International Search Report and Written Opinion of the International Searching Authority, PCT Application No. PCT/US2014/050298, Nov. 24, 2014, 13 pages.

(Continued)

*Primary Examiner* — Melissa Koval
*Assistant Examiner* — Rishi Patel
(74) *Attorney, Agent, or Firm* — Benjamin Fite; Fish & Richardson P.C.

(57) ABSTRACT

In some aspects, a downhole nuclear magnetic resonance (NMR) tool includes a magnet assembly and an antenna assembly. The NMR tool can operate in a wellbore in a subterranean region to obtain NMR data from the subterranean region. The magnet assembly produces a magnetic field in a volume about the wellbore. The antenna assembly produces excitation in the volume and acquires an azimuthally-selective response from the volume based on the excitation. The antenna assembly can include a transversal-dipole antenna and a monopole antenna.

26 Claims, 8 Drawing Sheets

(51) Int. Cl.
*G01R 33/36* (2006.01)
*G01R 33/38* (2006.01)

(56) References Cited

U.S. PATENT DOCUMENTS

| | | |
|---|---|---|
| 5,471,140 A | 11/1995 | Hanley |
| 5,543,711 A | 8/1996 | Srinivasan et al. |
| 5,557,201 A | 9/1996 | Kleinberg et al. |
| 5,705,927 A | 1/1998 | Sezginer et al. |
| 5,710,511 A | 1/1998 | Taicher et al. |
| 5,828,214 A | 10/1998 | Taicher et al. |
| 5,959,453 A | 9/1999 | Taicher et al. |
| 5,977,768 A | 11/1999 | Sezginer et al. |
| 6,051,973 A | 4/2000 | Prammer |
| 6,118,272 A | 9/2000 | Taicher et al. |
| 6,121,773 A | 9/2000 | Taicher et al. |
| 6,215,304 B1 | 4/2001 | Slade |
| 6,246,236 B1 | 6/2001 | Poitzsch et al. |
| 6,255,817 B1 | 7/2001 | Poitzsch et al. |
| 6,326,784 B1 | 12/2001 | Ganesan et al. |
| 6,373,248 B1 | 4/2002 | Poitzsch et al. |
| 6,703,833 B2 | 3/2004 | Wisler et al. |
| 7,463,027 B2 | 12/2008 | Prammer et al. |
| 7,733,086 B2 | 6/2010 | Prammer et al. |
| 2005/0030021 A1* | 2/2005 | Prammer et al. ............... 324/303 |
| 2005/0257610 A1* | 11/2005 | Gillen et al. ............... 73/152.02 |
| 2006/0255799 A1 | 11/2006 | Reiderman |
| 2009/0072825 A1 | 3/2009 | Prammer et al. |
| 2013/0018602 A1 | 1/2013 | Ong et al. |
| 2014/0117984 A1 | 5/2014 | Conrad et al. |
| 2015/0061664 A1* | 3/2015 | Reiderman et al. ............ 324/303 |

FOREIGN PATENT DOCUMENTS

| | | |
|---|---|---|
| WO | WO 00-14576 | 3/2000 |
| WO | WO2004/099817 | 11/2004 |

OTHER PUBLICATIONS

Halliburton, "MRIL-WD™ Magnetic Resonance Imaging Logging While Drilling Sensor," H02747, Jan. 2012, 2 pages.
Schlumberger, "proVISION Plus—Magnetic Resonance While Drilling", Copyright 2012, 7 pages.
Blanz et al., "Nuclear Magnetic Resonance Logging While Drilling (NMR-LWD): From an Experiment to a Day-to-Day Service for the Oil Industry", The Open-Access Journal for the Basic Principles of Diffusion Theory, Experiment and Application, 2010, 5 pages.
Schlumberger, "proVISION—Maximize Well Performance with Real-Time Reservoir Steering", Feb. 2003, 4 pages.
Extended European Search Report, EP Application No. EP14828119.9, Oct. 6, 2015, 7 pages.
PCT International Preliminary Report on Patentability, PCT/US2014/050298, Mar. 10, 2016, 9 pages.
Australian Government IP Australia, Patent Examination Report No. 1, May 2, 2016, 3 pages.
PCT International Preliminary Report on Patentability, PCT/US2014/050294, Mar. 10, 2016, 11 pages.

* cited by examiner

AZIMUTHALLY-SELECTIVE DOWNHOLE NUCLEAR MAGNETIC RESONANCE (NMR) TOOL

CROSS-REFERENCE TO RELATED APPLICATION

This application claims priority to U.S. Provisional Patent Application No. 61/872,362, filed on Aug. 30, 2013, entitled "Obtaining Nuclear Magnetic Resonance (NMR) Data from a Subterranean Region." The priority application is hereby incorporated by reference in this application.

BACKGROUND

This specification relates to azimuthally-selective downhole nuclear magnetic resonance (NMR) tools, for example, for obtaining NMR data from a subterranean region.

In the field of logging (e.g. wireline logging, logging while drilling (LWD) and measurement while drilling (MWD)), nuclear magnetic resonance (NMR) tools have been used to explore the subsurface based on the magnetic interactions with subsurface material. Some downhole NMR tools include a magnet assembly that produces a static magnetic field, and a coil assembly that generates radio frequency (RF) control signals and detects magnetic resonance phenomena in the subsurface material. Properties of the subsurface material can be identified from the detected phenomena.

DESCRIPTION OF DRAWINGS

Like reference symbols in the various drawings indicate like elements.

DETAILED DESCRIPTION

In some implementations, an NMR instrument can offer practical solutions for obtaining NMR data from the subsurface. In some instances, the instrument can provide a higher signal-to-noise ratio (SNR) (e.g., for a given DC power budget), motional immunity, azimuthal selectivity of measurements, or a combination of these or other advantages. In some cases, the instrument can be robust against environmental factors, and provide accurate or precise information for analysis of the subsurface.

Some example configurations for a downhole NMR instrument include a substantially two-dimensional (2D) transversal dipole arrangement for both the magnet assembly and the antenna assembly. The magnetic fields generated by the magnet and antennas can have axial homogeneity (i.e., homogeneity along the long axis of the NMR instrument) that is suitable for use during axial motion. In some cases, broader band excitation (saturation of nuclear magnetization) can be used, for example, to achieve axial symmetry (roundness) with this type of instrument. In some implementations, a downhole NMR tool is configured to generate axially-symmetric magnetic fields, with a magnet assembly generating a radial magnetic field and an antenna assembly generating a longitudinal RF magnetic field (also having a longitudinal sensitivity direction).

In some instances, an NMR instrument can produce a longitudinal static magnetic field in the volume of interest. In some examples, the instrument includes multiple transversal-dipole antennas (e.g., two identical transversal-dipole antennas) that produce circular polarized excitation and provide quadrature coil detection. An arrangement of multiple orthogonal antennas can be used, for example, with a longitudinal-dipole magnet that generates an axial static magnetic field in the volume of interest. In some examples, the instrument includes a multiple-volume arrangement that makes use of different regions of the magnet assembly to acquire the NMR signal. In some examples, a region of investigation has a shape that is suitable for measurements while tripping the drill string (i.e., transiting the drill string in the wellbore). Some example implementations include a combination of a transversal-dipole antenna axially-symmetrical response and a monopole antenna axially-symmetrical response, which can enable azimuthally-resolved unidirectional NMR measurements in some instances.

Figure 1A:
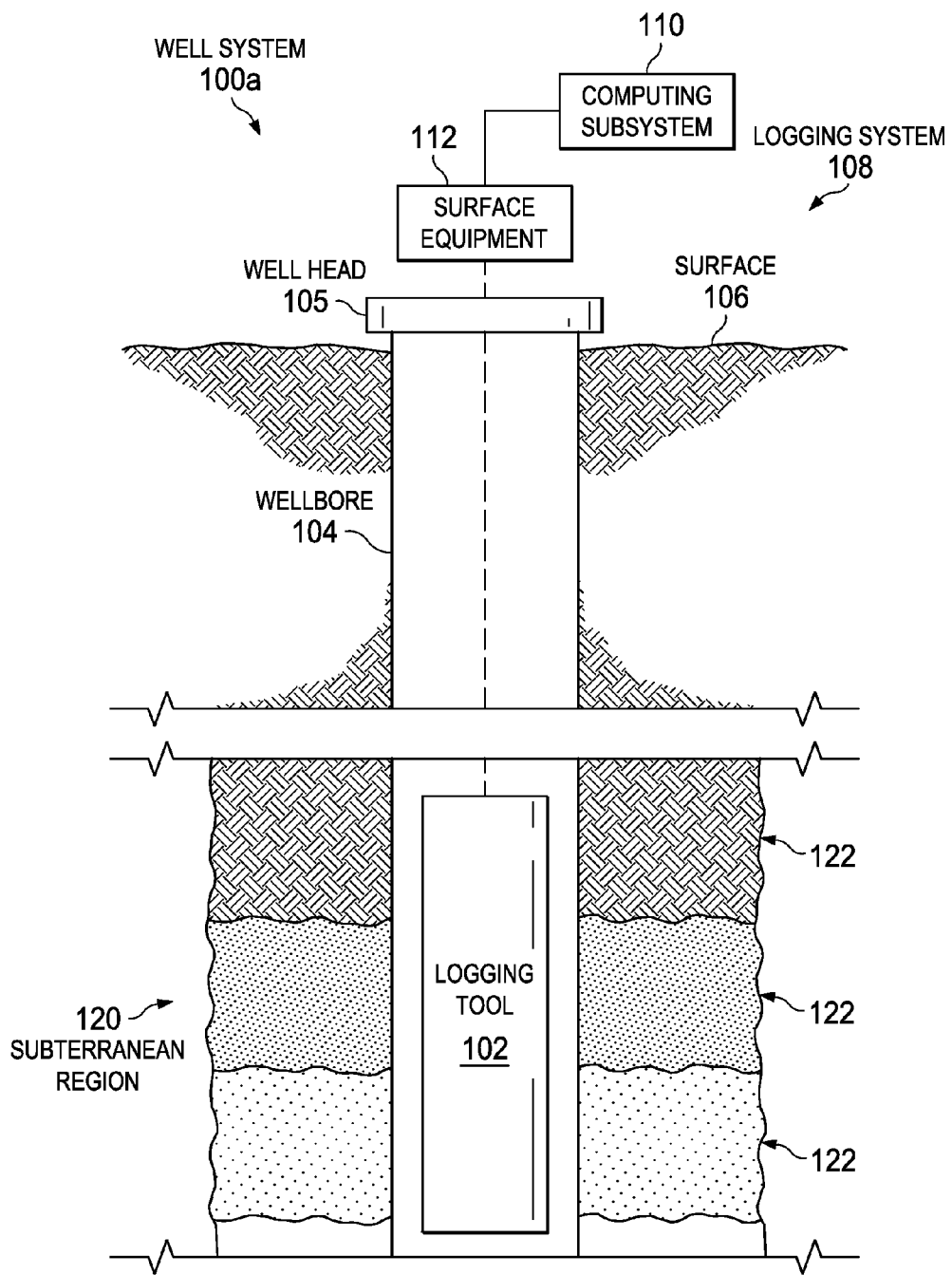
FIG. 1A is a diagram of an example well system.

FIG. 1A is a diagram of an example well system 100a. The example well system 100a includes an NMR logging system 108 and a subterranean region 120 beneath the ground surface 106. A well system can include additional or different features that are not shown in FIG. 1A. For example, the well system 100a may include additional drilling system components, wireline logging system components, etc.

The subterranean region 120 can include all or part of one or more subterranean formations or zones. The example subterranean region 120 shown in FIG. 1A includes multiple subsurface layers 122 and a wellbore 104 penetrated through the subsurface layers 122. The subsurface layers 122 can include sedimentary layers, rock layers, sand layers, or combinations of these and other types of subsurface layers. One or more of the subsurface layers can contain fluids, such as brine, oil, gas, etc. Although the example wellbore 104 shown in FIG. 1A is a vertical wellbore, the NMR logging system 108 can be implemented in other wellbore orientations. For example, the NMR logging system 108 may be adapted for horizontal wellbores, slanted wellbores, curved wellbores, vertical wellbores, or combinations of these.

The example NMR logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 110 can be implemented as a component of, or can be integrated with one or more components of, the surface equipment 112, the logging tool 102 or both. In some cases, the computing subsystem 110 can be implemented as one or more computing structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100a can include communication or telemetry equipment that allows communication among the computing subsystem 110, the logging tool 102, and other components of the NMR logging system 108. For example, the components of the NMR logging system 108 can each include one or more transceivers or similar apparatus for wired or wireless data communication among the various components. For example, the NMR logging system 108 can include systems and apparatus for optical telemetry, wireline telemetry, wired pipe telemetry, mud pulse telemetry, acoustic telemetry, electromagnetic telemetry, or a combination of these and other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

Figure 2A:
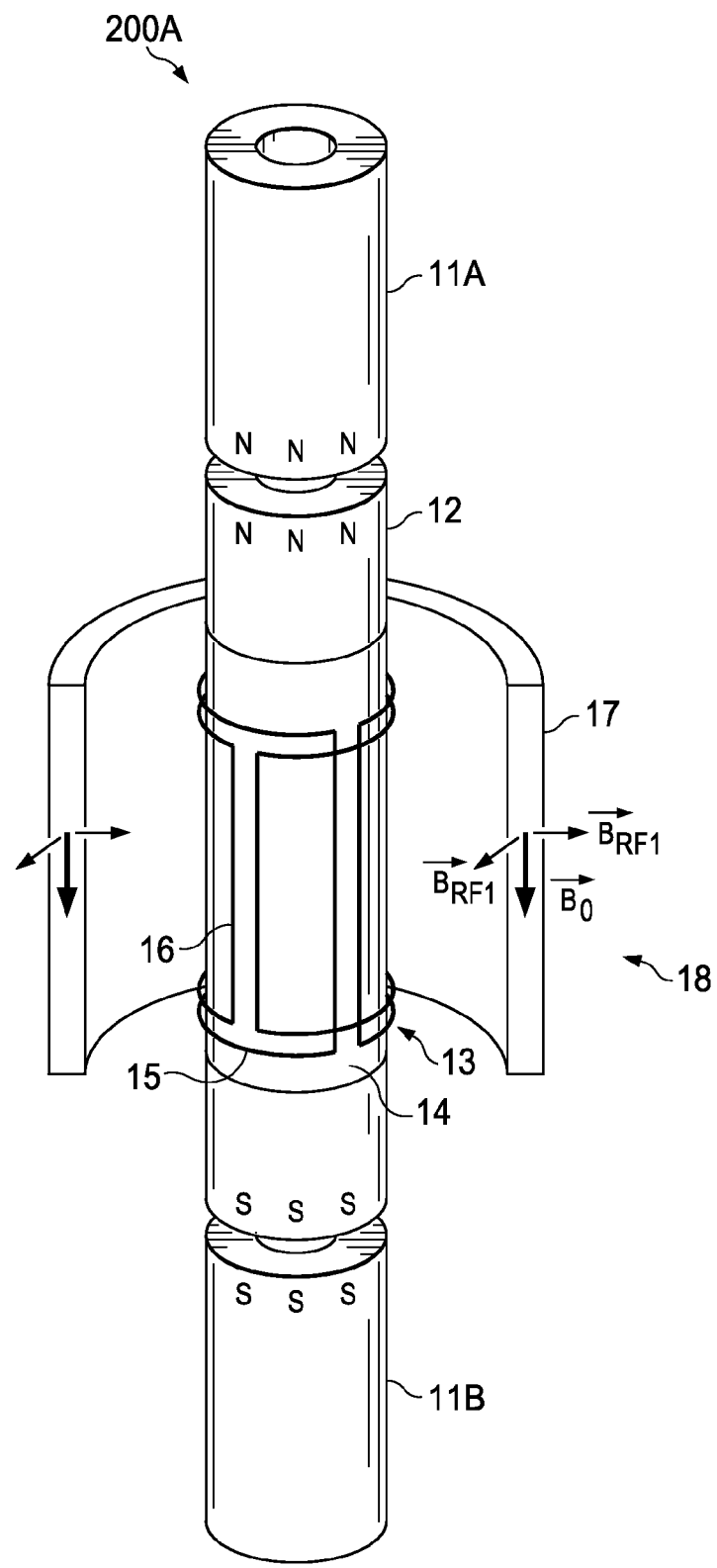
FIG. 2A is a diagram of an example downhole tool for obtaining NMR data from a subterranean region.
Figure 2B:
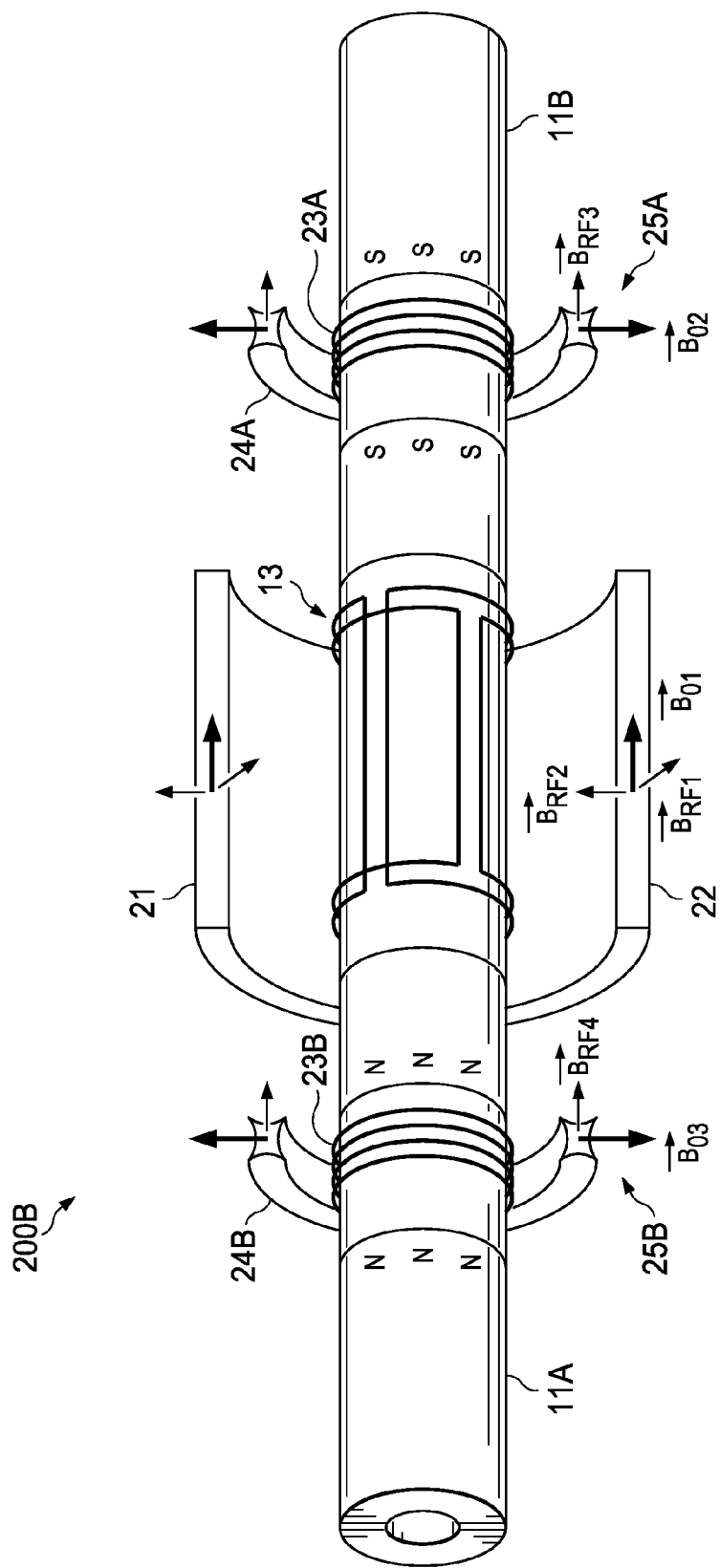
FIG. 2B is a diagram of another example downhole tool for obtaining NMR data from a subterranean region.

In some implementations, the logging tool 102 includes a magnet assembly that includes a central magnet and two end piece magnets. Examples are shown in FIGS. 2A, 2B, and 3B. The end piece magnets can be spaced apart from the axial ends of the central magnet. The end pieces together with the central magnets can define four magnetic poles, which may be arranged to enhance the static magnetic field in a volume of interest. In some cases, the central magnet defines a first magnetic field orientation, and the end piece magnets define a second magnetic field orientation that is orthogonal to the first magnetic field orientation. The logging tool 102 can also include multiple orthogonal transversal-dipole antennas. The orthogonal transversal-dipole antennas can produce circular polarized excitation in a subterranean volume and acquire a response from the volume by quadrature coil detection.

In some implementations, the logging tool 102 includes a magnet assembly that produces a magnetic field in multiple distinct sub-volumes in the subterranean region 120. An example is shown in FIG. 2B. A first sub-volume can be an elongate cylindrical-shell region that extends in the longitudinal direction (parallel to the wellbore axis), and the magnetic field in the first sub-volume can be substantially uniformly oriented along the longitudinal direction. Second and third sub-volumes can be spaced apart from the axial ends of the first sub-volume, and the static magnetic field in the second and third sub-volumes can have a radial orientation (perpendicular to the longitudinal direction). The second and third sub-volumes can be located at a different distance from the center of the tool string than the first volume. In some instances, the locations of the second and third sub-volumes allow the logging tool to collect information for mud filtrate invasion profiling. The logging tool 102 can also include multiple antenna assemblies at respective locations along the longitudinal axis. Each of the antenna assemblies can detect an NMR response from a respective one of the distinct sub-volumes.

In some implementations, the logging tool 102 includes a magnet assembly and a transversal-dipole and monopole antenna assembly. An example is shown in FIG. 3B. The transversal-dipole and monopole antenna assembly can obtain a unidirectional azimuthally-selective NMR response from a subterranean volume about the magnet assembly. The transversal-dipole and monopole antenna assembly can include orthogonal transversal-dipole antennas and a monopole antenna.

Figure 1B:
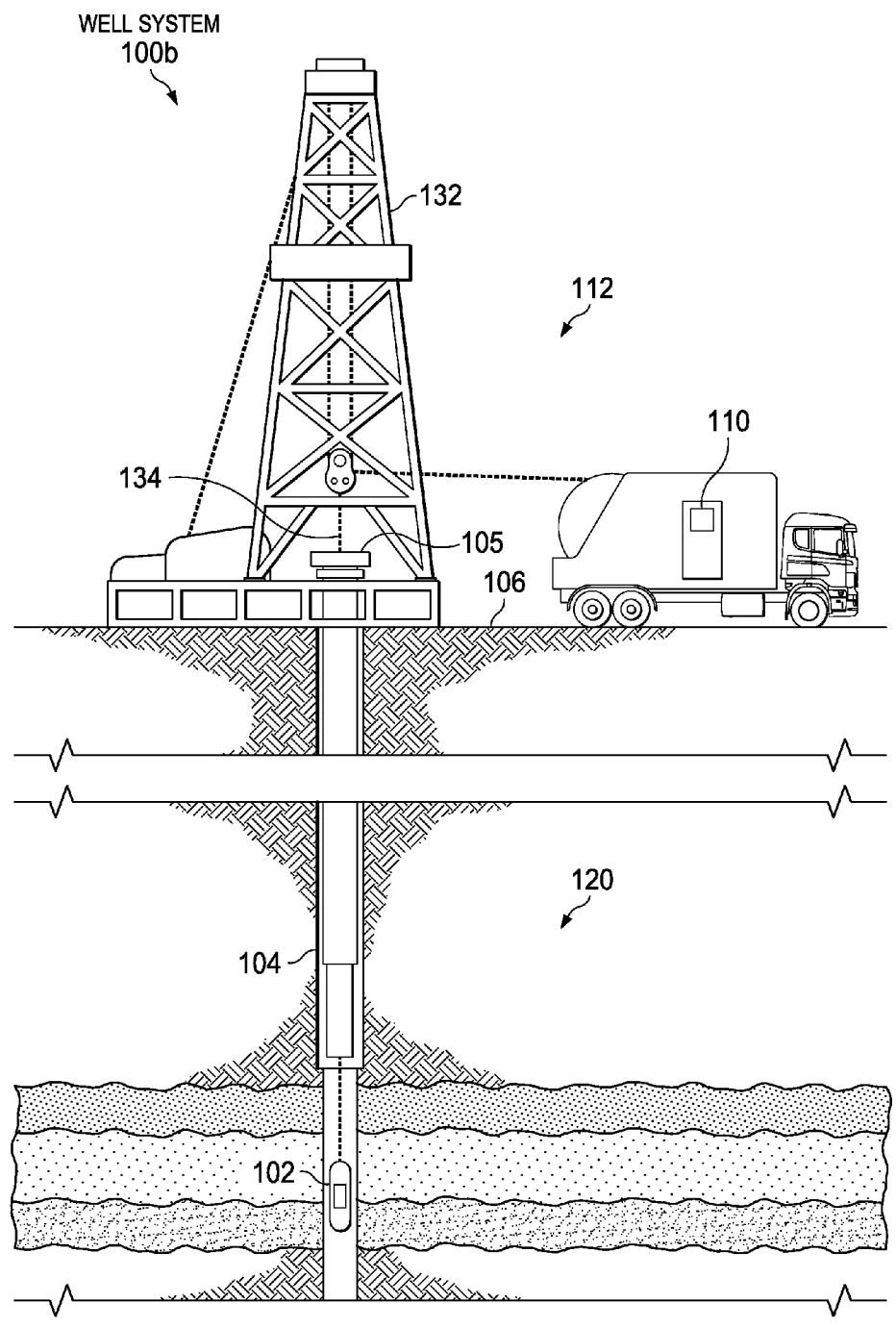
FIG. 1B is a diagram of an example well system that includes an NMR tool in a wireline logging environment.

In some examples, NMR logging operations are performed during wireline logging operations. FIG. 1B shows an example well system 100b that includes the logging tool 102 in a wireline logging environment. In some example wireline logging operations, the surface equipment 112 includes a platform above the surface 106 equipped with a derrick 132 that supports a wireline cable 134 that extends into the wellbore 104. Wireline logging operations can be performed, for example, after a drill string is removed from the wellbore 104, to allow the wireline logging tool 102 to be lowered by wireline or logging cable into the wellbore 104.

Figure 1C:
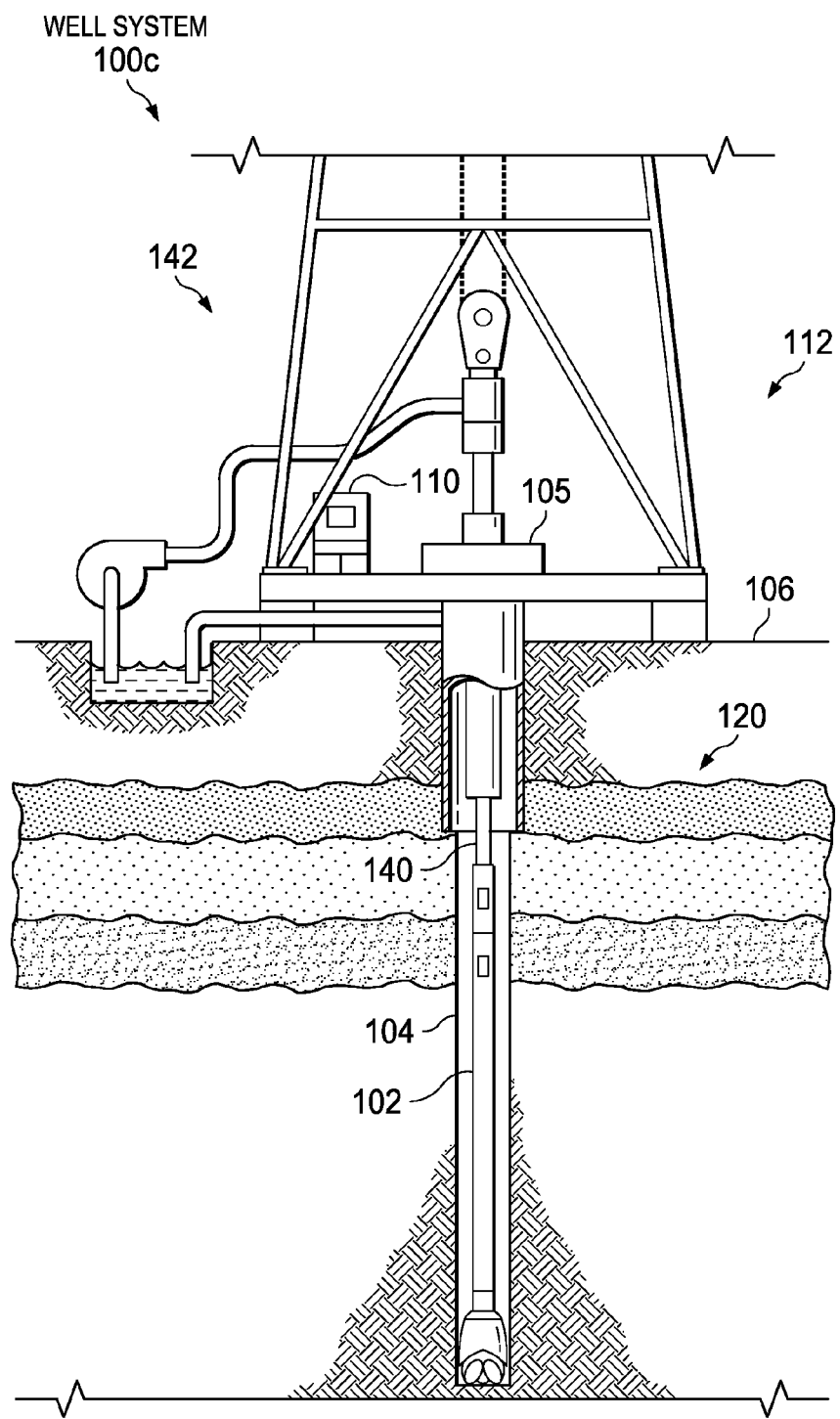
FIG. 1C is a diagram of an example well system that includes an NMR tool in a logging while drilling (LWD) environment.

In some examples, NMR logging operations are performed during drilling operations. FIG. 1C shows an example well system 100c that includes the logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, a kelly, drill pipe, a bottomhole assembly, and other components. The bottomhole assembly on the drill string may include drill collars, drill bits, the logging tool 102, and other components. The logging tools may include measuring while drilling (MWD) tools, LWD tools, and others.

In some implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest. In some example implementations, the logging tool 102 collects data while the drill string 140 is moving, for example, while it is being tripped in or tripped out of the wellbore 104.

In some implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, viscosity, porosity, material content, or other properties of the subsurface layers 122 based on the NMR measurements acquired by the logging tool 102 in the wellbore 104.

In some implementations, the logging tool 102 obtains NMR signals by polarizing nuclear spins in the subterranean region 120 and pulsing the nuclei with a radio frequency (RF) magnetic field. Various pulse sequences (i.e., series of radio frequency pulses, delays, and other operations) can be used to obtain NMR signals, including the Carr Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, a saturation recovery pulse sequence, and other pulse sequences.

The acquired spin-echo signals (or other NMR data) may be processed (e.g., inverted, transformed, etc.) to a relaxation-time distribution (e.g., a distribution of transverse relaxation times $T_2$ or a distribution of longitudinal relaxation times $T_1$), or both. The relaxation-time distribution can be used to determine various physical properties of the formation by solving one or more inverse problems. In some cases, relaxation-time distributions are acquired for multiple logging points and used to train a model of the subterranean region. In some cases, relaxation-time distributions are acquired for multiple logging points and used to predict properties of the subterranean region.

FIG. 2A is a diagram of an example NMR tool 200A. The example NMR tool 200A includes a magnet assembly that generates a static magnetic field to produce polarization, and an antenna assembly that (a) generates a radio frequency (RF) magnetic field to generate excitation, and (b) acquires NMR signals. In the example shown in FIG. 2A, the magnet assembly that includes the end piece magnets 11A, 11B and a central magnet 12 generates the static magnetic field in the volume of investigation 17. In the volume of investigation 17, the direction of the static magnetic field (shown as the solid black arrow 18) is parallel to the longitudinal axis of the wellbore. In some examples, a magnet configuration with double pole strength can be used to increase the strength of the magnetic field (e.g., up to 100-150 Gauss or higher in some instances).

In the example shown in FIG. 2A, the antenna assembly 13 includes two mutually orthogonal transversal-dipole antennas 15, 16. In some instances, the NMR tool 200A can be implemented with a single transversal-dipole antenna. For example, one of the transversal-dipole antennas 15, 16 may be omitted from the antenna assembly 13. The example transversal-dipole antennas 15, 16 shown in FIG. 2A are placed on an outer surface of a soft magnetic core 14, which is used for RF magnetic flux concentration. The static magnetic field can be axially symmetric (or substantially axially symmetric), and therefore may not require broader band excitation associated with additional energy loss. The volume of investigation can be made axially long enough and thick enough (e.g., 20 cm long, and 0.5 cm thick in some environments) to provide immunity or otherwise decrease sensitivity to axial motion, lateral motion, or both. A longer sensitivity region can enable measurement while tripping the drill string. The sensitivity region can be shaped by shaping the magnets 11A, 11B, 12 and the soft magnetic material of the core 14.

In some implementations, the antenna assembly 13 additionally or alternatively includes an integrated coil set that performs the operations of the two transversal-dipole antennas 15, 16. For example, the integrated coil may be used (e.g., instead of the two transversal-dipole antennas 15, 16) to produce circular polarization and perform quadrature coil detection. Examples of integrated coil sets that can be adapted to perform such operations include multi-coil or complex single-coil arrangements, such as, for example, birdcage coils commonly used for high-field magnetic resonance imaging (MRI).

Compared to some example axially-symmetrical designs, the use of the longitudinal-dipole magnet and the transversal-dipole antenna assembly also has an advantage of less eddy current losses in the formation and drilling fluid (i.e., "mud") in the wellbore due to a longer eddy current path than for some longitudinal-dipole antenna(s).

In some aspects, NMR measurements over multiple sub-volumes can increase the data density and therefore SNR per unit time. Multiple volume measurements in a static magnetic field having a radial gradient can be achieved, for example, by acquiring NMR data on a second frequency while waiting for nuclear magnetization to recover (e.g., after a CPMG pulse train) on a first frequency. A number of different frequencies can be used to run a multi-frequency NMR acquisition involving a number of excitation volumes with a different depth of investigation. In addition to higher SNR, the multi-frequency measurements can also enable profiling the fluid invasion in the wellbore, enabling a better assessment of permeability of earth formations. Another way to conduct multi-volume measurements is to use different regions of the magnet assembly to acquire an NMR signal. NMR measurements of these different regions can be run at the same time (e.g., simultaneously) or at different times.

FIG. 2B is a diagram of another example NMR tool 200B. The example NMR tool 200B also includes a magnet assembly that generates a static magnetic field to produce polarization, and an antenna assembly that (a) generates a radio frequency (RF) magnetic field to generate excitation, and (b) acquires NMR signals. In the example shown in FIG. 2B, the magnet assembly produces a magnetic field having a dominant axial component in the volume of investigation 21. The directions of the RF magnetic field (produced by two transversal dipole antennas as in FIG. 2A) and the static magnetic field in this region are shown at 22. In the example shown in FIG. 2B, two distinct volumes of investigation 24A, 24B are created near the magnet poles (beyond the axial ends of the central magnet) where the static magnetic field has a predominantly radial component. The example NMR antennas shown at 23A and 23B can generate RF magnetic fields in the volumes of investigation 24A and 24B near the longitudinal-dipole antennas. The longitudinal direction of the RF magnetic fields in the volumes of investigation 24A and 24B, and the radial direction of the static magnetic field in the volumes of investigation 24A and 24B, are shown at 25A and 25B.

In some aspects, a combination of transversal-dipole and monopole antennas can be used to enable unidirectional azimuthally-selective measurements, without substantially reducing SNR in some cases. In some examples, the NMR excitation can be substantially axially symmetric (e.g., using either the transversal-dipole antenna or the monopole antenna) while a combination of axially-symmetrical sensitivity transversal-dipole antenna and the axially-symmetrical sensitivity monopole antenna responses can enable azimuthally-resolved measurements.

Figure 3A:
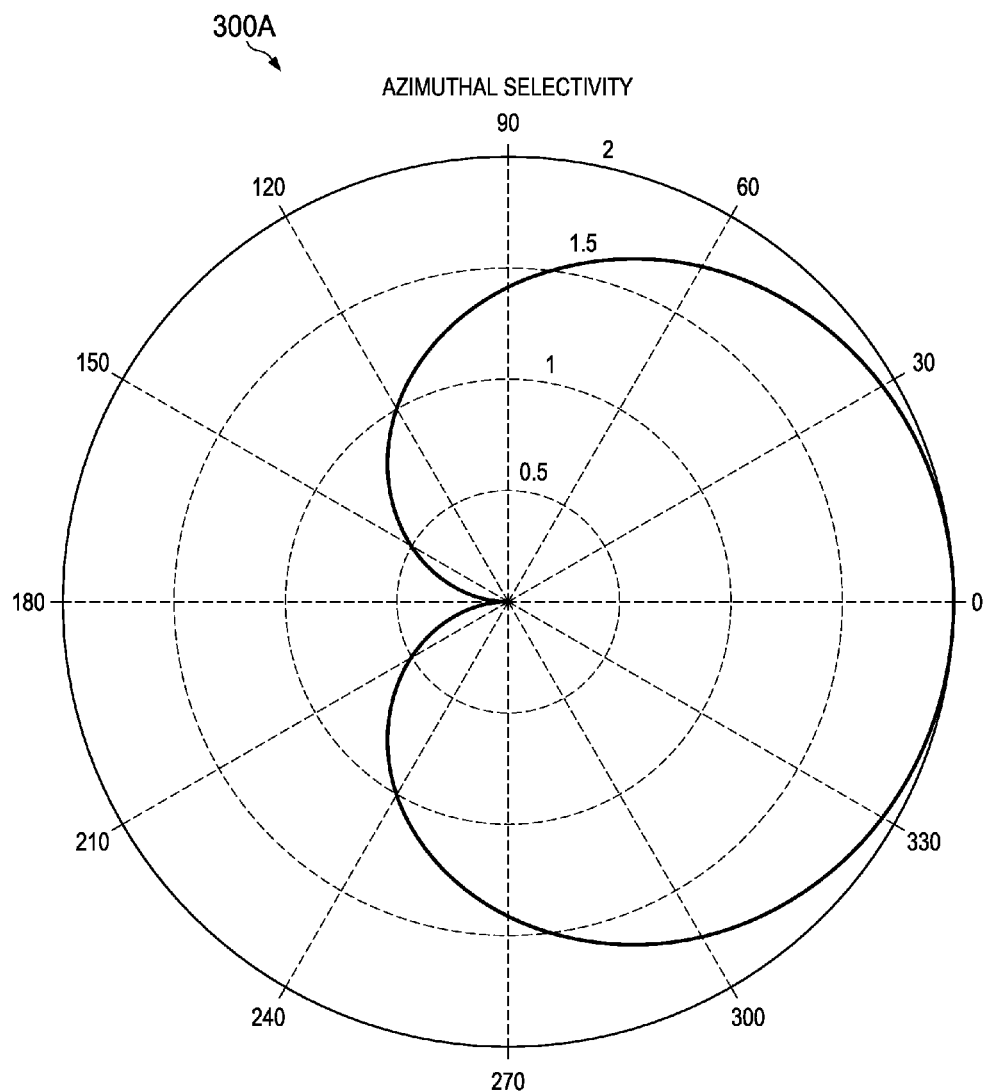
FIG. 3A is a plot showing azimuthal selectivity for an example downhole tool.
Figure 3B:
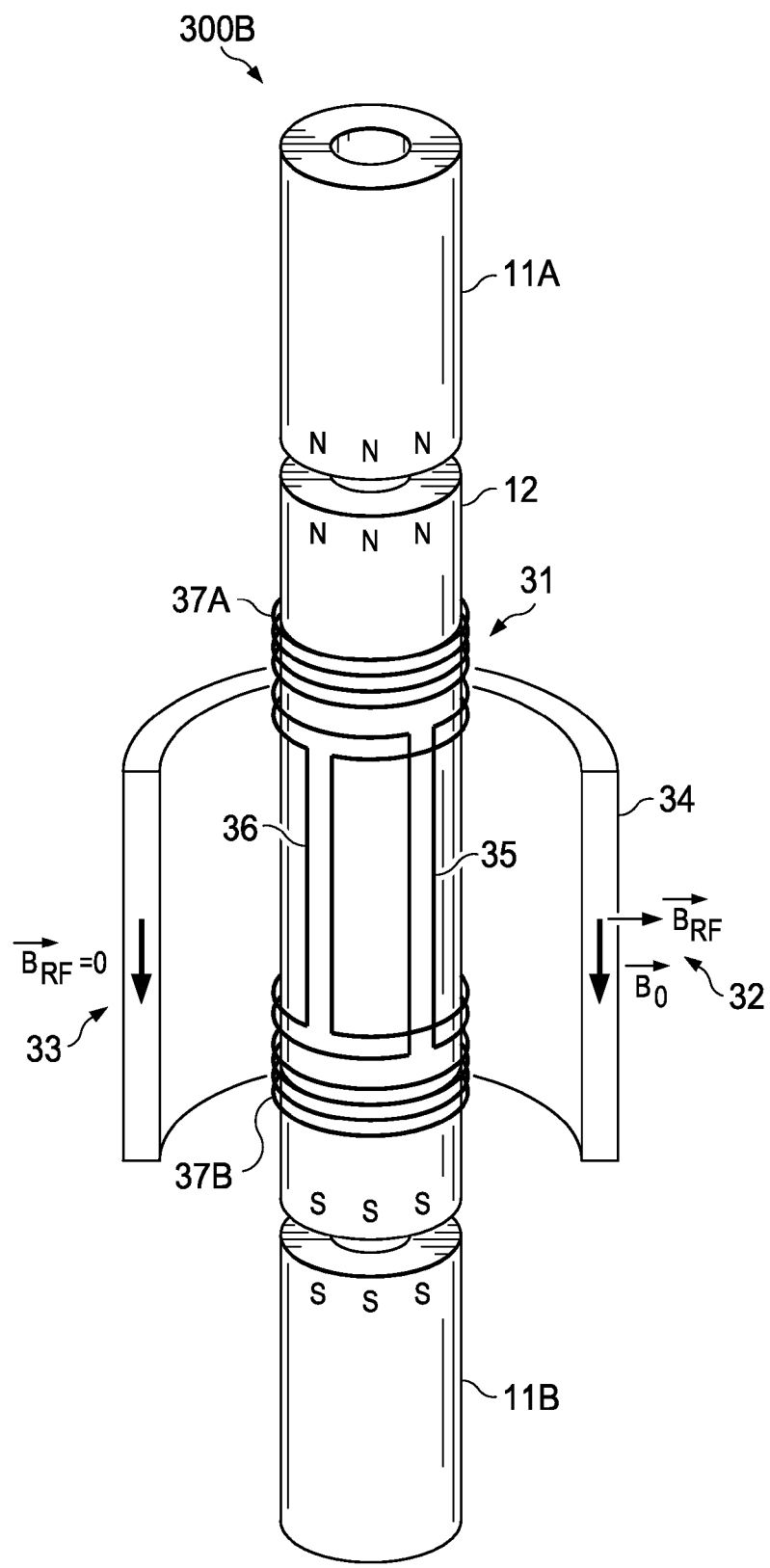
FIG. 3B is a diagram of another example downhole tool for obtaining NMR data from a subterranean region.

FIGS. 3A and 3B illustrate aspects of an example azimuthally-selective NMR tool. FIG. 3A is a plot 300A showing an example of azimuthally selected data from the example downhole tool 300B shown in FIG. 3B. The example NMR tool 300B includes a magnet assembly that generates a static magnetic field to produce polarization, and an antenna assembly that (a) generates a radio frequency (RF) magnetic field to generate excitation, and (b) acquires NMR signals. The antenna assembly 31 shown in FIG. 3B includes a monopole antenna and two orthogonal transversal-dipole antennas 35 and 36. The example monopole antenna includes two coils 37A and 37B connected in reverse polarity in order to generate a substantially radial RF magnetic field in the volume of investigation 34. Due to reciprocity, the same coil arrangement can have a radial sensitivity direction. The example RF magnetic fields BRF presented at 32 and 33 can reflect the total sensitivity direction when the monopole antenna response is combined with one of the transversal-dipole antenna responses.

The example monopole antenna shown in FIG. 3B includes an arrangement of coils that generate locally a substantially radially-directed magnetic field, i.e., the field that would be produced by a single "magnetic charge" or magnetic pole. Here, we use the term "monopole" to distinguish this type of magnetic field from a dipole magnetic field (transversal or longitudinal). In some cases, the monopole antenna assembly generates quasi-stationary (relatively low frequency) magnetic fields. In the example shown, the coils 37A and 37B, which are connected in reverse polarity, are two parts of one monopole antenna assembly. Each coil by itself can be implemented as a standard longitudinal antenna. A monopole antenna can be implemented in another manner.

The polar plot in FIG. 3A shows an example of the antenna sensitivity, demonstrating unidirectional azimuthal selectivity. A combination of the responses of each of the orthogonal transversal-dipole antennas with the response of the monopole antenna can give any of four possible directions covering all quadrants of the transversal plane. Rotation of the drill string while drilling may cause an amplitude modulation of the azimuthally selective response and therefore an amplitude modulation of the NMR relaxation signal (e.g., a CPMG echo train). The amplitude modulation parameters can indicate the azimuthal variations of the NMR properties (e.g., the NMR porosity variations).

The coils 37A and 37B of the example monopole antenna shown in FIG. 3B can be used in combination with transversal-dipole antennas 35 and 36, for example, to achieve azimuthal selectivity. Either of the coils 37A and 37B can also be used as a separate antenna (in addition to or without the transversal-dipole antennas 35, 36), for example, to gain SNR. In some cases, an NMR tool is implemented with a monopole antenna and a longitudinal magnet, without other antennas. For example, the transversal-dipole antennas 35 and 36 may be omitted from the antenna assembly 31 in some cases.

Figure 4A:
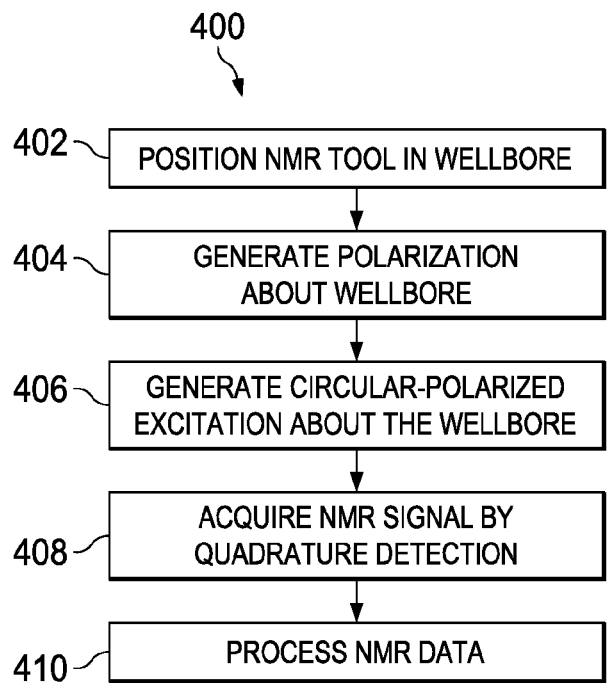
FIG. 4A is a flowchart showing an example technique for obtaining NMR data from a subterranean region.
Figure 4B:
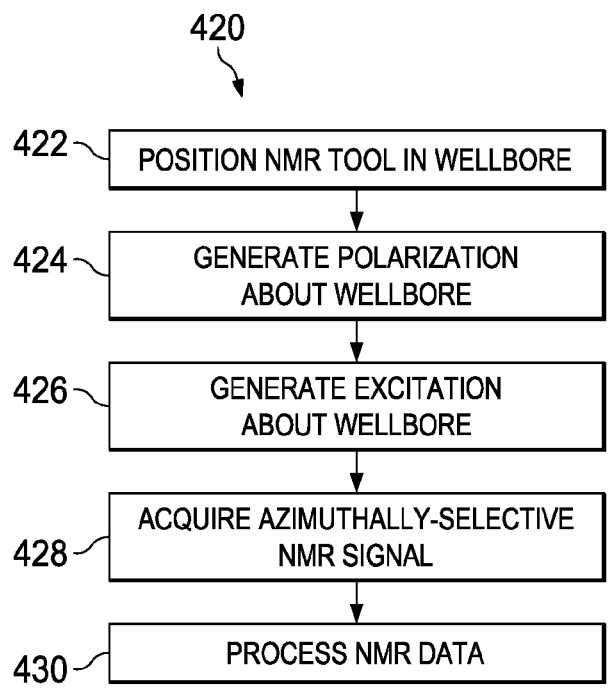
FIG. 4B is a flowchart showing another example technique for obtaining NMR data from a subterranean region.

FIG. 4A is a flowchart showing an example process 400 for obtaining NMR data from a subterranean region; and FIG. 4B is a flowchart showing another example process 420 for obtaining NMR data from a subterranean region. Each of the processes 400 and 420 can be performed independent of the other, or the processes 400 and 420 can be performed concurrently or in concert. For example, the processes 400 and 420 may be performed in series or in parallel, or one of the processes may be performed without performing the other.

The processes 400 and 420 can be performed by downhole NMR tools such as the example NMR tools 200A, 200B, or 300B shown in FIGS. 2A, 2B and 3B, or by another type of NMR tool. The processes 400 and 420 can be performed by a downhole NMR tool while the tool is disposed within a wellbore during well system operations. For example, the downhole NMR tool can be suspended in the wellbore for wireline logging (e.g., as shown in FIG. 1B), or the downhole NMR tool can be coupled to a drill string for NMR LWD (e.g., as shown in FIG. 1C).

Each of the processes 400 and 420 can include the operations shown in FIGS. 4A and 4B (respectively), or either of the processes can include additional or different operations. The operations can be performed in the order shown in the respective figures or in another order. In some cases, one or more of the operations can be performed in series or parallel, during overlapping or non-overlapping time periods. In some cases, one or more of the operations can be iterated or repeated, for example, for a specified number of iterations, for a specified time duration, or until a terminating condition is reached.

At 402 in the example process 400 shown in FIG. 4A, the NMR tool is positioned in a wellbore. In some cases, the NMR tool includes a magnet assembly to produce a magnetic field in a volume in the subterranean region about the wellbore. The volume can include, for example, all or part of any of the volumes of investigation 17, 21, 24A, 24B, 34 shown in FIG. 2A, 2B or 3B, or another volume of interest. Generally, the NMR tool includes a magnet assembly to polarize nuclear spins in the volume of interest, and an antenna assembly to excite the nuclear spins and to acquire an NMR signal based on the excitation.

At 404, polarization is generated in a volume about the wellbore. The polarization is generated by a static magnetic field, which is produced by the magnet assembly of the NMR tool in the wellbore. The polarization refers to the magnetic polarization of the nuclear spins in the volume. In other words, a portion of the nuclear spins becomes aligned with the static magnetic field, and the volume develops a bulk magnetic moment. In some cases, the static magnetic field is configured (e.g., by the shape and position of the magnet assembly) to produce longitudinal polarization (e.g., parallel to the long axis of the wellbore) or polarization having another orientation.

In some examples, the magnet assembly includes a central magnet (e.g., the central magnet 12 shown in FIGS. 2A, 2B, 3B, or another type of central magnet) and two end piece magnets (e.g., the end piece magnets 11A, 11B shown in FIGS. 2A, 2B, 3B, or another type of end piece magnet). In some cases, the magnets in the magnet assembly are permanent magnets. As shown, for example, in FIG. 2A, the central magnet can be an elongate permanent magnet having a first axial end and a second, opposite axial end, with the first end piece magnet spaced apart from the first axial end of the central magnet, and with the second end piece magnet spaced apart from the second axial end of the central magnet. In some cases, the two end piece magnets have a common magnetic field orientation, and the central magnet has the opposite magnetic field orientation (e.g., such that both end piece magnets have a magnetic field orientation that is orthogonal to the magnetic field orientation of the central magnet).

At 406, circular-polarized excitation is generated in the volume about the wellbore. The circular-polarized excitation is produced in the volume by an antenna assembly. For example, the antenna assembly can be energized by a radio-frequency current, which produces a radio-frequency (RF) magnetic field in the volume about the wellbore. The RF magnetic field generated by the antenna assembly manipulates the nuclear spins to produce an excited spin state that has circular polarization. In other words, the resulting spin polarization has a circular (or circumferential) orientation in the volume about the wellbore.

In some examples, the antenna assembly includes orthogonal transversal-dipole antennas. The antenna assembly 13 shown in FIGS. 2A and 2B and the antenna assembly 31 shown in FIG. 3B are examples of antenna assemblies that include two orthogonal transversal-dipole antennas. Each antenna 15, 16 in the example antenna assembly 13 can independently produce a transversal-dipole magnetic field, for example, by conducting radio-frequency current. In the examples shown, each transversal-dipole magnetic field has a transverse orientation with respect to the longitudinal axis of the NMR tool. In other words, the transversal-dipole magnetic field is oriented orthogonal to the long axis of the wellbore.

In the example shown, the transversal-dipole magnetic field produced by the antenna 15 is orthogonal to the transversal-dipole magnetic field produced by the other antenna 16. For example, in a Cartesian coordinate system of three mutually-orthogonal directions, the longitudinal axis of the NMR tool can be considered the "z" direction, and the transversal-dipole magnetic fields (produced by the antennas 15, 16) are oriented along the "x" and "y" directions, respectively.

In some implementations, other types of excitation are produced by the NMR tool. For example, in some cases, the circular-polarized excitation is produced in a first sub-volume (e.g., the volume of investigation 21 in FIG. 2B) by the orthogonal transversal-dipole antennas, and excitation having another orientation is produced in second and third sub-volumes (e.g., the volumes of investigation 24A, 24B in FIG. 2B) that are spaced apart from the axial ends of the first sub-volume. The excitation in the second and third sub-volumes can be produced, for example, by a longitudinal-dipole RF field generated by other antenna assemblies (e.g., by antennas 23A and 23B in FIG. 2B). The distinct sub-volumes may be useful for different purposes. For example, the first sub-volume can be elongate (parallel to the long axis of the wellbore), to acquire NMR data from the first sub-volume while the NMR tool moves along the wellbore (e.g., while tripping a drill string). In some cases, the other sub-volumes can be positioned to acquire NMR data for mud filtrate invasion profiling or other applications.

At 408, an NMR signal is acquired by quadrature coil detection. The NMR signal is based on the excitation generated at 406. The NMR signal can be, for example, an echo train, a free induction decay (FID), or another type of NMR signal. In some cases, the acquired NMR data includes T1 relaxation data, T2 relaxation data, or other data. The NMR signal can be acquired by the antenna assembly that produced the excitation or by another antenna assembly. In some cases, an NMR signal can be acquired in multiple sub-volumes.

Quadrature coil detection can be performed by the orthogonal transversal-dipole antennas. Quadrature coil detection can be performed by using two orthogonal coils, each picking up the signal induced by circular polarized nuclear magnetization (the signal in the coils have 90 degree phase difference). Even if during transmission only one coil is used (e.g., producing linear polarized RF magnetic field), the nuclear magnetization can still be circular polarized. Quadrature coil transmission (two orthogonal coils driven by RF currents having 90 degree phase difference) can enable circular polarized excitation, which can help to reduce power consumption compared to a linear polarized excitation in some cases. Quadrature coil detection can be used, for example, to increase signal-to-noise ratio (SNR) when exciting only one coil (not using circular polarized excitation to simplify hardware), or circular polarization can be used to save power while detecting signals with one coil. In some cases, both circular polarization and quadrature coil detection can be used to save power and increase SNR. In some cases, the use of circular polarization or quadrature coil detection (or both) is efficient when the mutually orthogonal antennas are substantially identical. This is possible in the example magnet/antenna configuration that has a longitudinal dipole magnet and two transversal antennae. Other configurations that have one of the two antennae less efficient than the other, although allowing for mutually orthogonal antennae, may not provide the same advantages in some cases.

At 410, the NMR data are processed. The NMR data can be processed to identify physical properties of the subterranean region or to extract other types of information. For example, the NMR data may be processed to identify density, viscosity, porosity, material content, or other properties of the subterranean region about the wellbore.

At 422 in the example process 420 shown in FIG. 4B, the NMR tool is positioned in a wellbore, and at 424 polarization is generated in a volume about the wellbore. Operations 422 and 424 in FIG. 4B are similar to operations 402 and 404 shown in FIG. 4A. For example, the NMR tool includes a magnet assembly to polarize nuclear spins in the volume of interest, and an antenna assembly to excite the nuclear spins and to acquire an NMR signal based on the excitation. The polarization can be produced at 424 in the manner described with respect to operation 404 of FIG. 4A and by the same type of magnet assembly; or polarization can be produced at 424 in another manner or by another type of magnet assembly.

At 426, excitation is generated in a volume about the wellbore. The excitation is produced in the volume by an antenna assembly. For example, the antenna assembly can be energized by a radio-frequency current, which produces a radio-frequency (RF) magnetic field in the volume about the wellbore. The RF magnetic field generated by the antenna assembly manipulates the nuclear spins to produce an excited spin state. In some instances, the spin state has a higher excitation in a selected azimuthal direction, such that the level of spin excitation varies along a circular (or circumferential) direction about the wellbore, for example, due to an azimuthally-selective RF magnetic field.

In some examples, the antenna assembly includes a transversal-dipole and monopole antenna assembly. The antenna assembly 31 shown in FIG. 3B is an example of an antenna assembly that includes a transversal-dipole and monopole antenna assembly. In the example shown in FIG. 3B, the transversal-dipole and monopole antenna assembly includes two orthogonal transversal-dipole antennas 35 and 36 in a central region, and a monopole antenna that includes a first coil 37A at a first axial end of the transversal-dipole antennas 35 and 36 and a second coil 37B at a second, opposite axial end of the transversal-dipole antennas 35 and 36; the coils 37A and 37B of the monopole antenna are arranged with opposite polarity.

At 428, an azimuthally-selective NMR signal is acquired. The NMR signal is based on the excitation generated at 426. The NMR signal can be, for example, an echo train, a free induction decay (FID), or another type of NMR signal. In some cases, the acquired NMR data includes T1 relaxation data, T2 relaxation data, or other data. The NMR signal can be acquired by the antenna assembly that produced the excitation or by another antenna assembly. In some cases, the NMR signal is acquired by an antenna assembly having azimuthally-selective sensitivity, such as, a transversal-dipole and monopole antenna assembly.

In some implementations, the azimuthally-selective NMR signal is acquired as a combination of multiple NMR signal acquisitions. The signal acquisitions can include, for example, acquisitions by one or more transversal-dipole antennas and one or more monopole antennas. The signals can be combined to enable azimuthally-resolved measurements of the volume about the wellbore. For example, in some cases, a proper combination of the responses of each of the orthogonal transversal-dipole antennas with the response of the monopole antenna can give any of four possible directions covering all quadrants of the transversal plane.

At 430, the NMR data are processed. The NMR data can be processed to identify physical properties of the subterranean region or to extract other types of information. For example, the NMR data may be processed to identify density, viscosity, porosity, material content, or other properties of the subterranean region about the wellbore. In some cases, the NMR data are processed to identify azimuthal variations in the subterranean region about the wellbore. For example, rotating the NMR tool may cause an amplitude modulation of the azimuthally-selective response. The amplitude modulation parameters can indicate the azimuthal variations of the properties affecting the NMR signal (e.g., porosity, density, viscosity, material content, etc.).

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of examples have been described. Nevertheless, it will be understood that various modifications can be made. Accordingly, other implementations are within the scope of the following claims.

The invention claimed is:

1. A nuclear magnetic resonance (NMR) tool for use in a wellbore in a subterranean region, the NMR tool comprising:
   a magnet assembly to produce a magnetic field in a volume in a subterranean region; and
   an antenna assembly to produce an excitation in the volume, and to acquire an azimuthally-selective response from the volume based on the excitation, the antenna assembly comprising a transversal-dipole antenna and a monopole antenna,
   wherein the antenna assembly is configured so that the NMR tool acquires the azimuthally-selective response from the volume using both the transversal-dipole antenna and the monopole antenna.

2. The NMR tool of claim 1, wherein the monopole antenna comprises: a first coil at a first axial end of the transversal-dipole antenna; and a second coil at a second, opposite axial end of the transversal-dipole antenna, and the first and second coils are oriented along a common axis and have opposite polarity.

3. The NMR tool of claim 1, wherein the excitation is produced by the transversal-dipole antenna and the monopole antenna.

4. The NMR tool of claim 1, wherein the magnet assembly comprises: a central magnet having a first axial end and a second, opposite axial end; a first end piece magnet spaced apart from the first axial end of the central magnet; and a second end piece magnet spaced apart from the second axial end of the central magnet.

5. The NMR tool of claim 4, wherein the magnet assembly comprises a permanent magnet assembly, and the central magnet and the first and second end piece magnets each comprise one or more permanent magnets.

6. The NMR tool of claim 4, wherein the central magnet defines a first magnetic field orientation, and the first and second end piece magnets each define a second magnetic field orientation that is orthogonal to the first magnetic field orientation.

7. The NMR tool of claim 1, wherein the magnet assembly and the transversal-dipole antenna and a monopole antenna are configured to operate within a wellbore in the subterranean region during drilling operations.

8. The NMR tool of claim 1, wherein:
   the volume comprises multiple distinct sub-volumes, the multiple distinct sub-volumes comprise a first sub-volume that is elongate in a first direction parallel to a longitudinal axis of the NMR tool, the magnetic field in the first sub-volume being substantially uniformly oriented in the first direction; and
   the NMR tool further comprises multiple additional antenna assemblies at respective locations along the longitudinal axis, each antenna assembly to detect an NMR response from a respective one of the distinct sub-volumes.

9. The NMR tool of claim 1, wherein the magnet assembly and antenna assembly are operable to acquire an NMR signal while drilling.

10. A method of obtaining nuclear magnetic resonance (NMR) data from a subterranean region, the method comprising:
   producing a magnetic field in a volume in a subterranean region by a magnet assembly in a wellbore; and
   producing an excitation in the volume; and
   acquiring an azimuthally-selective response from the volume based on the excitation, the response acquired by an antenna assembly comprising a transversal-dipole antenna and a monopole assembly,
   wherein the antenna assembly is configured so that a NMR tool acquires the azimuthally-selective response from the volume using both the transversal-dipole antenna and the monopole antenna.

11. The method of claim 10, further comprising identifying azimuthal variations in the volume based on the response.

12. The method of claim 10, wherein:
   the antenna assembly further comprises additional transversal-dipole antennas;
   the monopole antenna comprises a first coil at a first axial end of the transversal-dipole antennas, and a second coil at a second, opposite axial end of the transversal-dipole antennas; and
   the first and second coils are oriented along a common axis and have opposite polarity.

13. The method of claim 12, wherein the excitation is produced by at least one of the monopole antenna or one or more of the transversal-dipole antennas.

14. The method of claim 10, wherein a downhole NMR tool comprises the magnet assembly and the antenna assembly, and the excitation is produced and the response is acquired while the downhole NMR tool is disposed in a wellbore in the subterranean region.

15. The method of claim 14, wherein the NMR tool is coupled to a drill string and operates during drilling operations in the wellbore.

16. A drill string assembly comprising a downhole Nuclear Magnetic Resonance (NMR) tool disposed in a wellbore in a subterranean region, the downhole NMR tool comprising:
a magnet assembly to produce a magnetic field in a volume in a subterranean region; and
a transversal-dipole and monopole antenna assembly to obtain an NMR response from the volume,
wherein the transversal-dipole and monopole antenna assembly is configured so that the NMR tool acquires the NMR response from the volume using both a transversal-dipole antenna and a monopole antenna.

17. The drill string assembly of claim 16, wherein the transversal-dipole and monopole antenna assembly is operable to obtain a unidirectional azimuthally-selective NMR response from the volume.

18. The drill string assembly of claim 16, wherein the downhole NMR tool comprises multiple transversal-dipole orthogonal antennas to:
produce circular polarized excitation in a first sub-volume; and
acquire a response from the first sub-volume by quadrature coil detection.

19. The drill string assembly of claim 16, wherein:
the volume comprises multiple distinct sub-volumes, the multiple distinct sub-volumes comprise a first sub-volume that is elongate in a first direction parallel to a longitudinal axis of the downhole NMR tool, and the magnetic field in the first sub-volume is substantially uniformly oriented in the first direction; and
the downhole NMR tool further comprises multiple additional antenna assemblies at respective locations along the longitudinal axis, each antenna assembly operable to detect an NMR response from a respective one of the distinct sub-volumes.

20. A nuclear magnetic resonance (NMR) tool for use in a wellbore in a subterranean region, the NMR tool comprising:
a magnet assembly to produce a magnetic field in a volume in a subterranean region, the magnetic field in the volume oriented parallel to a longitudinal axis of the NMR tool; and
an antenna assembly to produce an excitation in the volume and to acquire a response from the volume based on the excitation, the antenna assembly comprising a monopole antenna,
wherein the antenna assembly is configured so that the NMR tool acquires the response from the volume using both the transversal-dipole antenna and the monopole antenna.

21. The NMR tool of claim 1, wherein the transversal-dipole antenna and the monopole antenna each have a substantially axially-symmetrical excitation.

22. The NMR tool of claim 21, wherein a combination of substantially axially-symmetrical response of the transversal-dipole antenna and monopole antenna enable the azimuthally-selective response from the volume.

23. The NMR tool of claim 16, wherein the transversal-dipole antenna and the monopole antenna each have a substantially axially-symmetrical excitation.

24. The NMR tool of claim 23, wherein a combination of substantially axially-symmetrical response of the transversal-dipole antenna and monopole antenna enable the NMR response from the volume.

25. The NMR tool of claim 20, wherein the transversal-dipole antenna and the monopole antenna each have a substantially axially-symmetrical excitation.

26. The NMR tool of claim 25, wherein a combination of substantially axially-symmetrical response of the transversal-dipole antenna and monopole antenna enable the response from the volume.

* * * * *